(12) United States Patent
Davis et al.

(10) Patent No.: US 9,138,286 B2
(45) Date of Patent: Sep. 22, 2015

(54) ULTRASOUND DETECTABLE INTERVENTIONAL MEDICAL DEVICE

(75) Inventors: John M. Davis, Richmond, VA (US); Patrick J. LePivert, Jupiter, FL (US)

(73) Assignee: Nuvue Therapeutics, Inc., Bristow, VA (US)

( * ) Notice: Subject to any disclaimer, the term of this patent is extended or adjusted under 35 U.S.C. 154(b) by 1406 days.

(21) Appl. No.: 12/288,427

(22) Filed: Oct. 20, 2008

(65) Prior Publication Data

US 2010/0286528 A1    Nov. 11, 2010

(51) Int. Cl.
*A61B 18/14*    (2006.01)
*A61B 19/00*    (2006.01)
*A61B 10/02*    (2006.01)
*A61B 18/02*    (2006.01)

(52) U.S. Cl.
CPC ......... *A61B 18/1477* (2013.01); *A61B 10/0233* (2013.01); *A61B 18/02* (2013.01); *A61B 2019/5425* (2013.01); *A61B 2019/5429* (2013.01)

(58) Field of Classification Search
CPC ............... A61B 2019/5425; A61B 2019/5429; A61B 2019/5263; A61B 8/0833; A61B 8/0841; A61B 8/4461; A61B 8/4466; A61B 17/34
USPC .......................................... 600/461, 466, 562
See application file for complete search history.

(56) References Cited

U.S. PATENT DOCUMENTS

| | | | |
|---|---|---|---|
| 4,249,539 A | 2/1981 | Vilkomerson et al. | |
| 5,095,910 A | 3/1992 | Powers | |
| 5,329,927 A | 7/1994 | Gardineer et al. | |
| 5,343,865 A * | 9/1994 | Gardineer et al. | 600/461 |
| 5,967,991 A | 10/1999 | Gardineer et al. | |
| 5,968,085 A * | 10/1999 | Morris et al. | 607/116 |
| 6,053,871 A | 4/2000 | Cockburn et al. | |
| 6,520,916 B1 * | 2/2003 | Brennen | 600/463 |
| 2004/0230111 A1 | 11/2004 | Smith et al. | |
| 2006/0049720 A1 | 3/2006 | Henderson et al. | |

* cited by examiner

*Primary Examiner* — Adam J Eiseman
(74) *Attorney, Agent, or Firm* — McHale & Slavin, P.A.

(57) ABSTRACT

An interventional medical device for use with a motion-sensitive ultrasonic imaging system comprising a flexible elongated member for insertion into soft tissue, a two-axis, flexing mechanism coupled to the flexible elongated member and a mechanism for controlled electrical excitation of the flexible elongated member. Each of the axial flexing mechanisms, when acted upon by electrical excitation, forcibly bends the elongated member along a section of it length causing its tip to move in the plane of the applied bending force. As a direct result of direct energy coupling by bending rather than vibration, the relative phases of the two axes can be controlled to accomplish specific movement of the tip of the flexible elongated member.

18 Claims, 7 Drawing Sheets

ULTRASOUND DETECTABLE INTERVENTIONAL MEDICAL DEVICE

FIELD OF THE INVENTION

The present invention relates to medically useful diagnostic or therapeutic probes and more particularly to such probes whose location within the body are accurately determinable using ultrasound.

BACKGROUND OF THE INVENTION

Ultrasound imaging is currently widely used by the medical profession to view internal soft human tissue. It is used to examine internal organs and to locate and examine abnormal and diseased tissue such as malignant tumors. With the advent of so-called "Doppler" (color) ultrasound equipment, vascular imaging became possible, as this equipment is able to sense the slight frequency shifts in reflected ultrasonic emissions caused by the movement of blood and it solid constituents. This and other improvements in ultrasound technology have enhanced it usefulness in recent years.

The use of ultrasound imaging as the primary or preferred monitoring system during, for example, minimally invasive surgical procedures such as fine needle biopsies, has become more prevalent as the use of ultrasound have become more widespread. The health advantages to the patient over, for example X-ray imaging techniques, however, have been somewhat offset by the shortcoming that needles and other small instruments are virtually invisible to ultrasound imaging systems. The medical professional has a critical need to be able to accurately see and locate the position of surgical instruments or treatment options such as those utilized in brachytherapy relative to target tissue. Several patents that recognized these needs have been issued.

U.S. Pat. No. 4,249,539 to Vilkomerson et al. describes a system which includes an omnidirectional ultrasonic transducer located at a needle tip. The transducer can be used either as a receiver of signals from the imaging transducer or as both receiver and transmitter. This system achieves the objective of visibility but has the disadvantage that the ultrasound equipment electronics must be designed to interact with the transducer and that the transducer must be inserted into the body.

U.S. Pat. No. 5,095,910 to Powers describes a system that includes and inner solid element that reciprocates longitudinally at audio frequencies within a hollow member. The use of this motion to achieve visibility, inspired by an effect first noticed by ultrasound practitioners, is described. The invention requires that the member, which may be a hollow needle for aspiration, contain the reciprocating member to remain visible. The system, by design, displays the tip rather than the whole needle, thus denying the operator the ability to observe neither the angle of entry nor the proximity of the needle to vital tissue such as nerve tissue or arteries.

U.S. Pat. No. 5,329,927 to Gardineer et al. describes a color ultrasonic imaging system for visualizing the tip of an interventional medical device such as a biopsy needle in the body of a patient. The patent describes an apparatus and method for generating a periodic or oscillating mechanical motion in the form of flexural waves in the X, Y and Z axes in the needle. This results in the generation of a significant Doppler shift effect that enables the needle to be detected by a color ultrasonic imaging system. The needle is made to oscillate by a mechanical motion mechanism or VIBER coupled thereto. The needle is coupled and secured to the mechanism using a flexible clip-like element formed from any suitable metal or plastic material. The flexible clip-like element is designed to accommodate and secure needles of different gauges to the mechanical motion inducing mechanism. Problems, however, having to do with assured fixation or attachment of the needle to the mechanical motion mechanism arise due to the fixed diameter of the flexible clip-like element which works well only with a narrow range of needle gauges. Moreover, the mechanical motion mechanism is generally very expensive to manufacture.

U.S. Pat. No. 5,967,991 to Gardineer et al. describes a disposable, single-element piezoelectric vibrating device. The driving method taught by this patent includes a vibrating piezoelectric element that couples its energy into an elongated member by means of a coupling bracket. The frequency of the piezoelectric element excitation is then varied to match the natural resonance frequency of the biopsy needle so as to induce a maximum vibration at it tip. As the resonant frequency of the needle can vary according to the density and elasticity of it environment (surrounding tissue) this method can require frequent operator adjustment. The single element produces vibrations primarily in one plane, requiring the operator to rotate the needle at times to maintain its visibility. As a practical matter, the problem of tailoring the natural resonance frequencies of all biopsy needles of various lengths and gauges is difficult in mass production.

Finally, U.S. Pat. No. 6,053,871 to Cockburn et al. describes the generation and transmission of an oscillating motion of an air column to the tip of a needle so that the location of the tip is visible by a color Doppler U.S. scanner. The oscillating system is made of a loud speaker, an amplifier, a separate signal generator and tubing connecting the amplifier to the needle hub. The system suffers from such limitations as the relative inefficiency of the loud speaker with regard to the generating sufficient motion into various tissues, the need for a design that prevents tissue from entering the needle while allowing the signal to exit, and the presence of connecting tubes that may limit manipulation of the needle.

Thus, there remains a need for a practical and more versatile medical device with it own built-in high quality, low cost vibrating assembly to accomplish the objectives envisioned by Gardineer et al. in U.S. Pat. No. 5,967,991.

OBJECTS OF THE INVENTION

It is therefore an object of the present invention to provide a self-contained ultrasonically detectable probe for insertion into the body.

It is another object of the present invention to provide a compact disposable self-contained ultrasonically detectable probe for insertion into the body.

SUMMARY OF THE INVENTION

According to the present invention, there is provided a medical device for use with a motion-sensitive ultrasonic imaging system comprising an elongated member for insertion into soft tissue, a two-axis, non-vibrational flexing mechanism coupled to the member and a mechanism for controlled excitation of the flexing mechanism. Each of the axial flexing mechanisms, when acted upon by electrical excitation, forcibly bends the elongated member along a section of it length causing its tip to move in the plane of the applied bending force. As a direct result of direct energy coupling by bending rather than vibration, the relative phases of the two axes can be controlled to accomplish specific movement of the tip. In one preferred embodiment of the present invention, electrical excitation of the two flexing mechanisms is quadrature-phased so as to cause the tip of the elongated member to orbit about its longitudinal axis. This orbital rotation ensures that motional energy is evenly distributed to the surrounding environment at all angles about the longitudinal axis.

DETAILED DESCRIPTION

Figure 1:
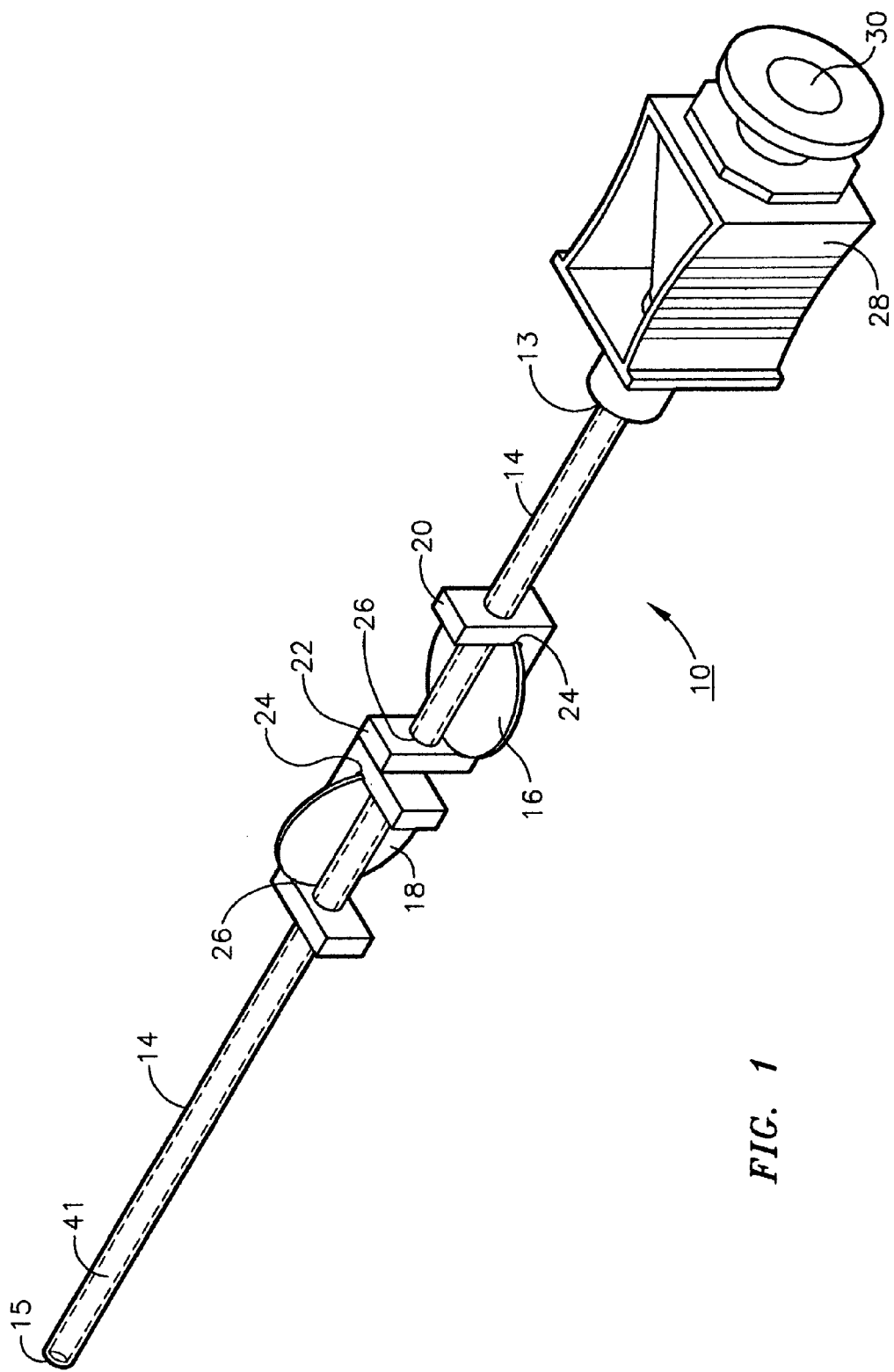
FIG. 1 is a perspective view of the mechanically activated elongated member of the device of the present invention including the bending elements.

As used herein, the following terms shall have the meanings defined herein. An interventional device or probe is meant to refer to any device that is used to perform an interventional medical procedure such as access, drainage, injection, ablation, biopsy and/or combinations of these procedures. The list of interventional devices may include but is not limited to: wires, cannula, introducers, needles of any type, probes for ablation such as cryoneedles, radiofrequency needles, injection needles, tissue handling, characterization and manipulation devices, etc. Interventional procedures may comprise of any direct, percutaneous, endoscopic, endovascular, endoluminal techniques that allow for the interventional device or probe to be guided and inserted into target tissue with precision and accuracy through ultrasonic tracking. Such procedures as generally referred to a minimally invasive and do not necessarily imply the use of surgical openings. Common interventional procedures include, but are not limited to: soft-tissue biopsy, access, drainage, injection, ablation, and/or characterization. The term target tissue is meant to include any part, organ or lesion of the animal or human body that can be seen with an ultrasound device.

According to the present invention, there is provided an interventional medical device or probe for use with a motion-sensitive ultrasonic imaging system comprising a flexible elongated member for insertion into soft tissue, a pair of non-vibrational, axially oriented, flexing mechanisms coupled to the flexible member and a mechanism for controlled electrical excitation of the axial flexing mechanisms. Each of the axial flexing mechanisms, when acted upon by electrical excitation, forcibly bends the flexible elongated member along a section of it length causing its tip to move in the plane of the applied bending force. As a direct result of direct energy coupling by bending rather than vibration, the relative phases of the two axes can be controlled to accomplish specific movement of the tip. In the preferred embodiment of the present invention, electrical excitation of the two flexing mechanisms is quadrature-phased so as to cause the tip of the elongated member to generally orbit about its longitudinal axis. This generally orbital movement ensures that motional energy is evenly distributed to the surrounding environment at all angles about the longitudinal axis.

The desired response to the motion of the elongated member is the local agitation of the various fluids and/or tissues surrounding the elongated member. This agitation is visible on an ultrasound system sensitive to motion. The magnitude of this effect is greatly affected by the elasticity, viscosity and density of the surrounding medium and by physical stresses on the elongated member. According to a further preferred embodiment of the present invention, the frequency of the electrical excitation is rapidly varied in a linear sweep of audible frequencies. This "spread-spectrum" approach maximizes the probability that adequate acoustical energy will be coupled to the surrounding medium at all times, independent of the elasticity, density or viscosity of the surrounding medium and that at least some portion of the resulting velocities caused within the surrounding medium will be selected to be displayed by the particular ultrasound detector and its internal filters.

Referring now to the accompanying drawings that depict one embodiment of the device of the present invention, the core 10 of the device 12 (see FIGS. 2 and 3) of the present invention comprises a flexible elongated member 14 including a tip 15 mechanically coupled (in the embodiment depicted in the various accompanying Figures, through physical contact) to a pair of bending elements 16 and 18 oriented orthogonally to one another. Each of bending elements 16 and 18 is retained against elongated element 14 by means of insulating retaining clips 20 and 22 respectively that, while allowing for transmission of vibrational mechanical energy to elongated member 14, insulate the balance of device 12 from the effects of such vibrational energy. Each of insulating retaining clips 20 and 22 includes an arcuate top and bottom 24 and 26 to limit non-bending movement of bending elements 16 and 18. Flexible elongated member 14 is permanently or removably mounted to a hub 28 having an aperture 30 therein. The purpose of hub 28 is primarily to serve as a connection point for an overlying housing 32 that surround the other necessary elements of device 12 as described hereinafter (see FIGS. 2 and 3) and to serve as resistance for extremity 13 of flexible member 14 when acted upon by bending elements 16 and 18 (thus allowing for generally orbital movement of tip 15), while aperture 30 serves as the insertion point for a stylet, cap needle, syringe or other similar device as described below in connection with the description of FIG. 3, or for access to passageway 41 in flexible member 14 described below in the case where device 12 is utilized for an aspiration or biopsy procedure requiring the removal of a tissue or other sample in the area of tip 15 via passageway 41 in flexible member 14. The purpose of housing 32 is to protect the sensitive electronic and piezoelectric components of device 12 and to provide a mechanism/handle for manual manipulation of device 12.

Figure 2:
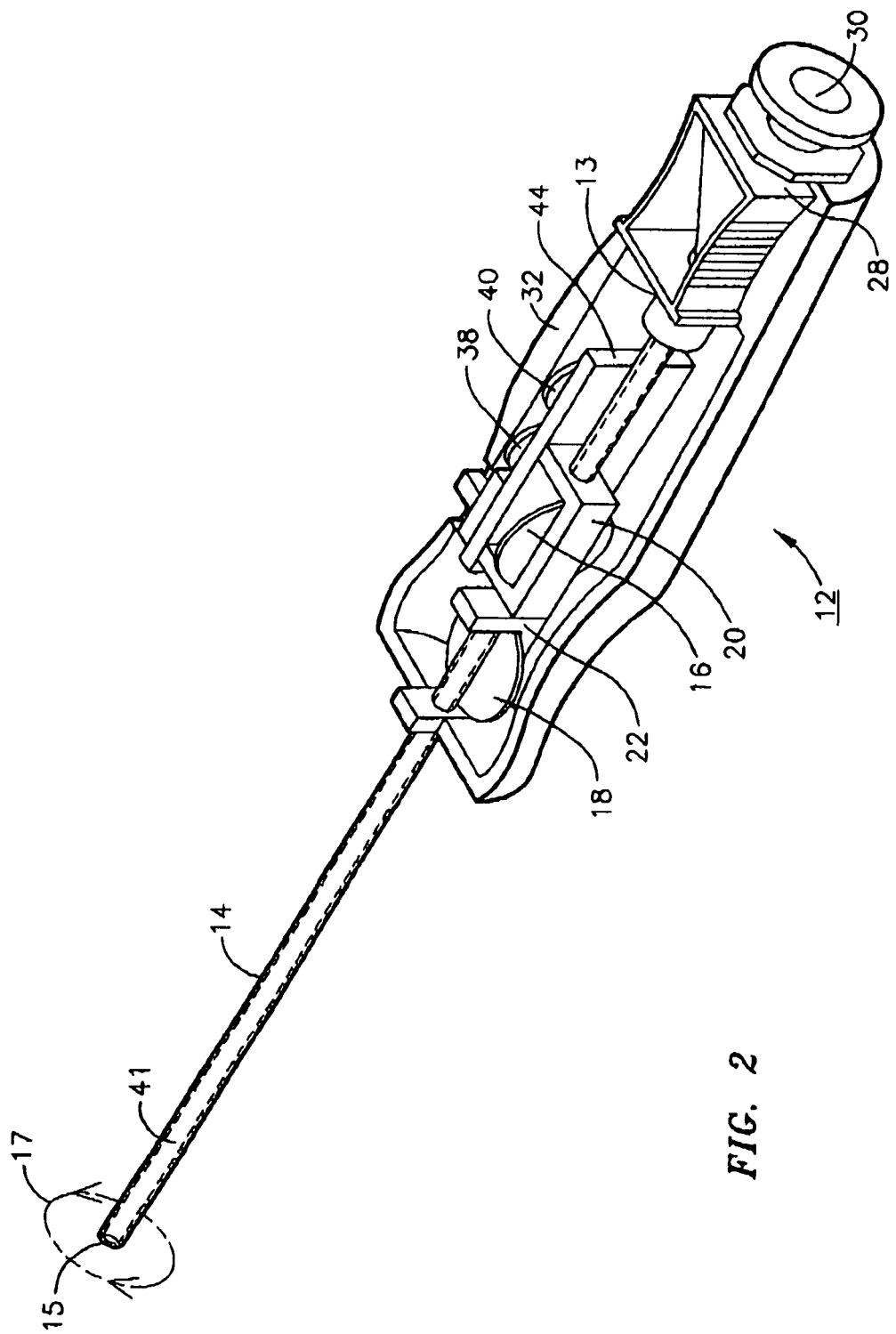
FIG. 2 is a cutaway view of the ultrasonically detectable device of the present invention.

Bending elements 16 and 18 comprise piezoelectric discs or elements that, when subjected to an electrical charge, deform mechanically causing flexible elongated element 14 to flex as described above. Since bending elements 16 and 18 are oriented orthogonally to one another and in physical contact with elongated element 14, they cause elongated element 14 to move orthogonally as each of them is caused to alter shape (vibrate) by the application of electrical energy thereto. Such orthogonal movement of elongated element 14 induces a generally orbital movement to tip 15 as depicted in FIG. 2 by arrow 17. Since, as described more fully below, the phase of the energy induced to vibrate bending elements 16 and 18 can be reversed, tip 15 can be rotated in two opposite generally orbital paths as depicted by the two directional arrow shown in FIG. 2. This ability to reverse the generally orbital rotation of tip 15 is of particular use in biopsy procedures where the ability to reverse the rotation of tip 15 may allow for the acquisition of relatively larger samples of tissue without relocation of tip 15 in the tissue target. Tip motion, as just described, may ease needle penetration, and/or fluid diffusion through tissue during injection procedures, and also provide tissue structure stimulation during specific procedures such as stimulation.

Electrical energy is imparted to bending elements 16 and 18 from batteries 38 and 40 (or similar energy providing drivers) via circuit board 44, with connection between bending elements 16 and 18 and batteries 38 and 40 being initiated by depression of switch 42. The waveform of the vibration of bending elements 16 and 18 as induced by the application of varying impulses of electrical energy from batteries 38 and 40 is controlled by the action of circuit board 44 that alters the frequency of vibration of bending elements 16 and 18 by varying the electrical energy supplied thereto from batteries 38 and 40. Circuit board 44 includes appropriate circuitry to provide: frequency, amplitude, waveform and phase inversion of the electronic signals transmitted to bending elements 16 and 18. Phase inversion will induce reversal of the direction of generally orbital movement 17 of tip 15 as depicted schematically in FIG. 2. The design and fabrication of such frequency, amplitude and waveform generator circuitry is well known in the art and no further description thereof is required herein to allow the skilled artisan to successfully practice the present invention.

Flexible elongated member 14 preferably comprises a needle of hollow shape. Such a hollow configuration that includes an elongated passage 41 running the entire interior length of elongated member 14, permits the injection of fluids, substances, mixtures of materials such as a radioactive seed in the case of brachytherapy treatment or the extraction/aspiration of tissue or the like in the case of a biopsy. In the latter instance, in order that elongated member/hollow needle 14 can be inserted to a point of interest, for example a tumor or the like, without preliminary collection of tissue that is not of interest during insertion, a stylet 46 is inserted through aperture 30 in hub 28 and passes through interior passage 41 of needle/elongated member 14 to plug interior passage 41 of needle 14 until it has reached the point of aspiration whereupon stylet 46 is withdrawn and aspiration, biopsy etc. performed.

Figure 4:
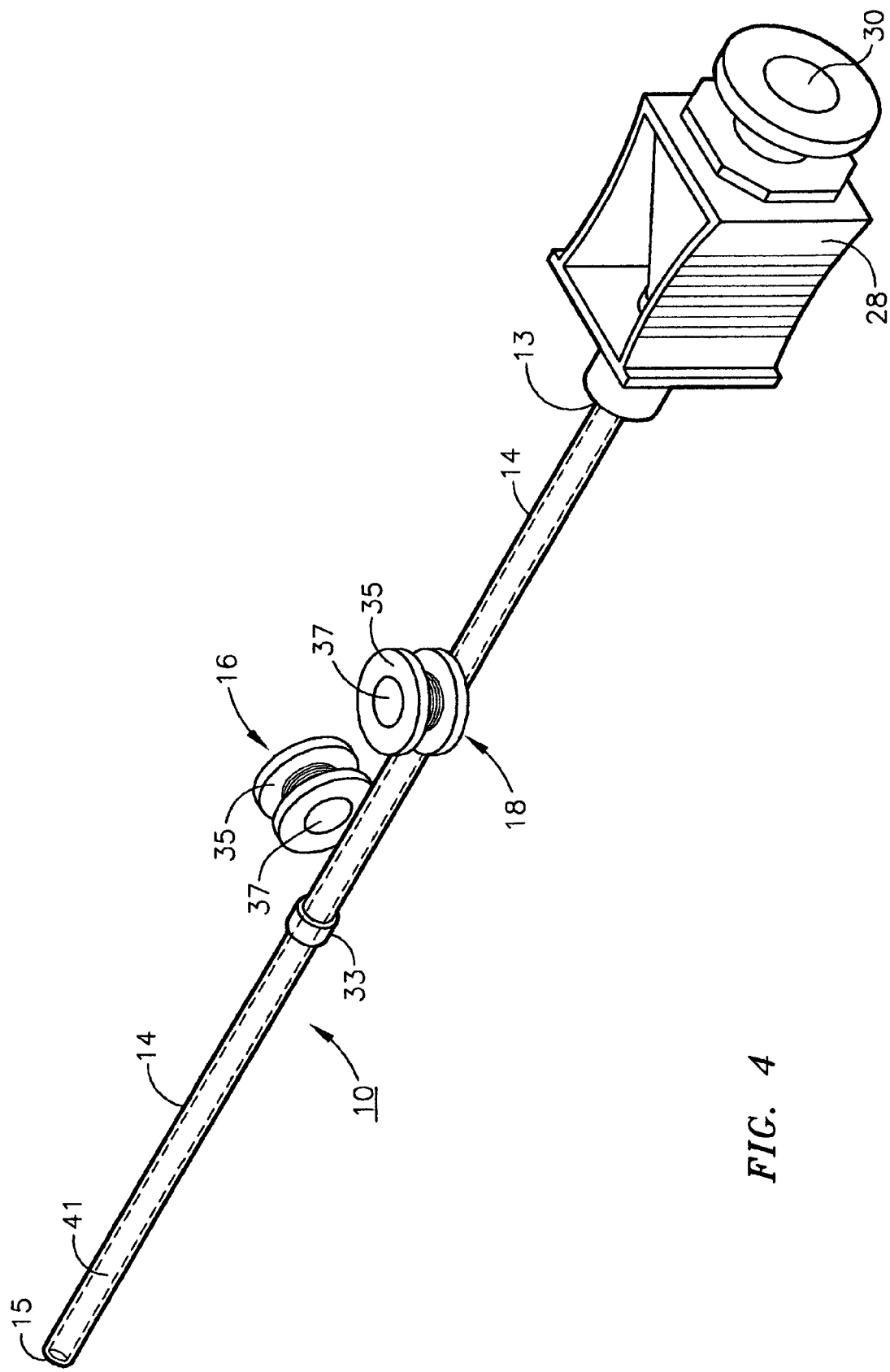
FIG. 4 is a perspective view of an alternative preferred embodiment of the mechanically activated elongated member of the device of the present invention including the bending elements.
Figure 5:
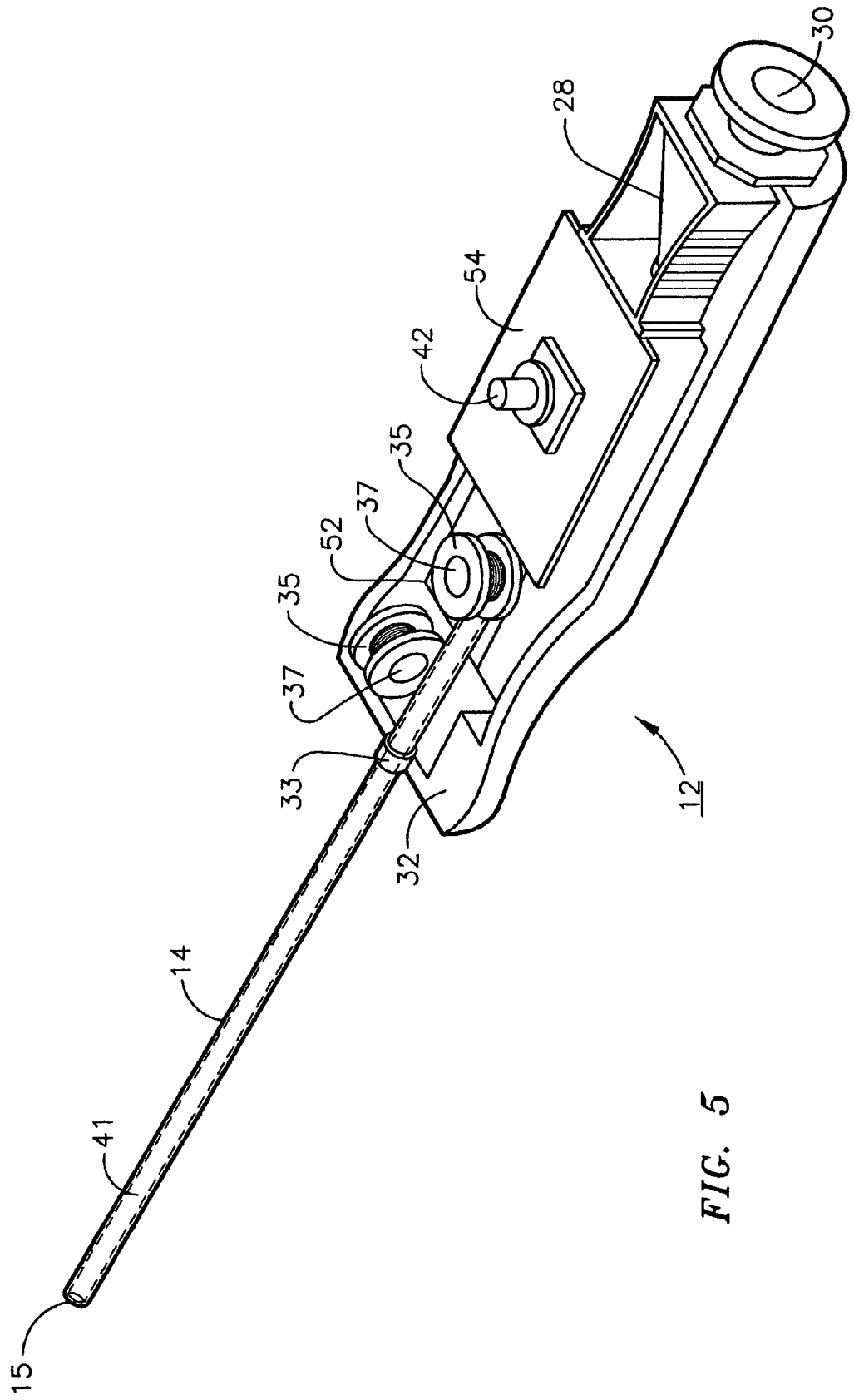
FIG. 5 is a cutaway view of the alternative preferred embodiment of the ultrasonically detectable device depicted in FIG. 4.
Figure 6:
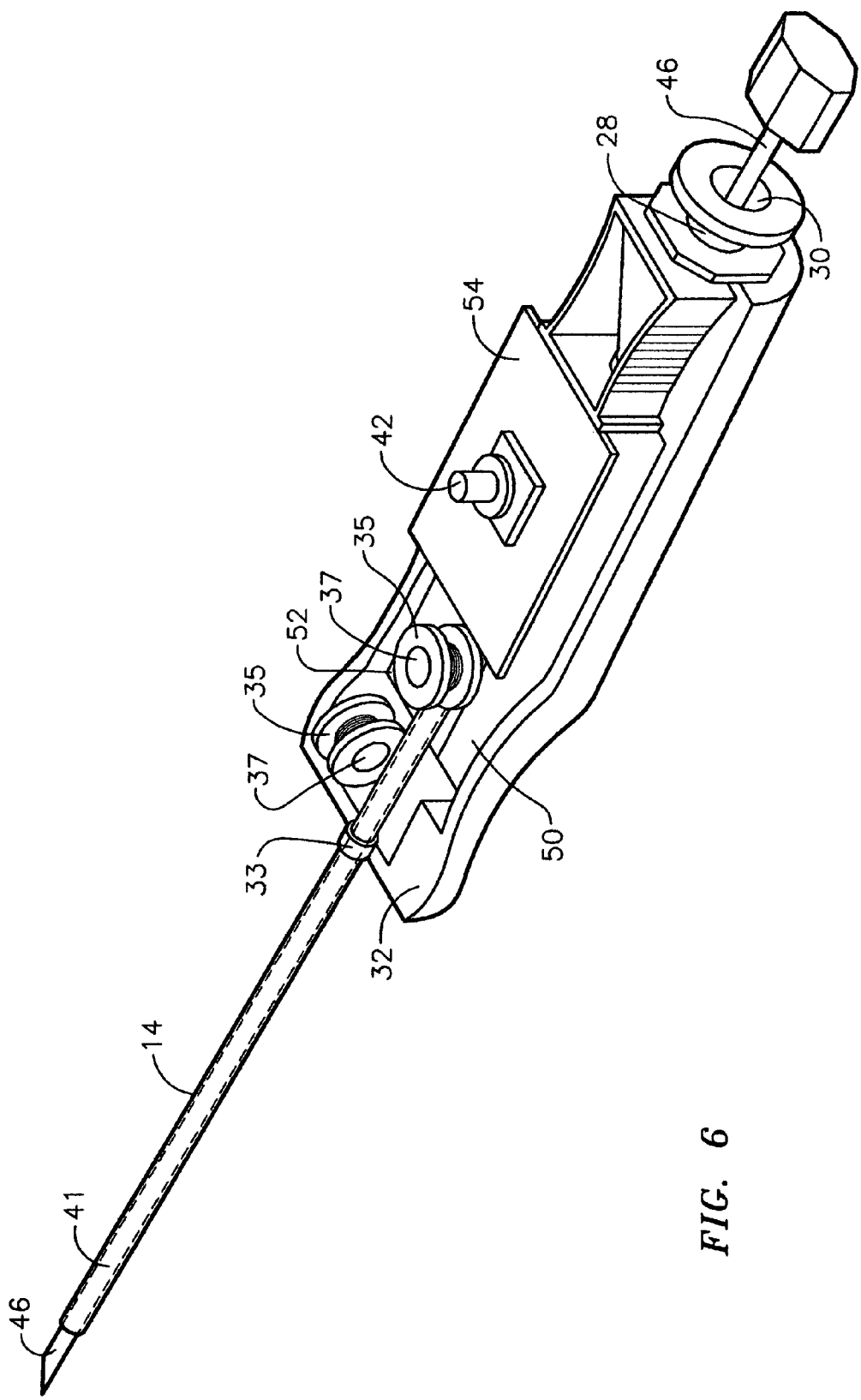
FIG. 6 is a cutaway view of the ultrasonically detectable device depicted in FIG. 5 having a stylet inserted therein.

Referring now to accompanying FIGS. 4-6 that depict a preferred embodiment of the device of the present invention, the core 10 of the device 12 (see FIGS. 5 and 6) of the present invention comprises a flexible elongated member 14 including a tip 15 mechanically coupled (in the embodiment depicted in the various accompanying Figures, through physical contact) to a pair of bending elements 16 and 18 oriented orthogonally to one another. Each of bending elements 16 and 18 is retained against elongated element 14 by means of suitable insulating retaining mechanisms (not shown in FIGS. 4-6) that, while allowing for transmission of vibrational mechanical energy to elongated member 14, insulate the balance of device 12 from the effects of such vibrational energy. Flexible elongated member 14 is mounted to a hub 28 having an aperture 30 therein. The purpose of hub 28 is primarily to serve as a connection point for an overlying housing 32 that surround the other necessary elements of device 12 as described hereinafter (see FIGS. 5 and 6) and to serve as resistance or an anchoring point for extremity 13 of flexible member 14 when acted upon by bending elements 16 and 18 (thus allowing for generally orbital movement of tip 15), while aperture 30 serves as the insertion point for a stylet or other similar device as described below in connection with the description of FIG. 6, or for access to passageway 41 in flexible member 14 described below in the case where device 12 is utilized for an aspiration or biopsy procedure requiring the removal of a tissue or other sample in the area of tip 15 via passageway 41 in flexible member 14. The purpose of housing 32 is to protect the sensitive electronic and driving components of device 12 and to provide a mechanism/handle for manual manipulation of device 12.

Also shown in FIGS. 4-6 is an elastomeric constraint 33 about flexible member 14. Elastomeric constraint 33 may comprise one or more individual elements. The purpose of elastomeric constraint 33 is to seal the interior of housing 32 from the infiltration of bodily fluids or other contaminants during use while also providing a fulcrum against which flexible member 14 is flexed as it is acted upon by bending elements 16 and 18 as described in greater detail below. It is important to note that elastomeric constraint 33 must not damp or otherwise negatively affect flexing of flexible member 14. Thus, according to a highly preferred embodiment of the present invention, constraint 33 comprises a material having a Shore A durometer of about 35.

According to the preferred embodiment depicted in FIGS. 4-6, bending elements 16 and 18 comprise coil driven magnets that, when subjected to an electrical charge, cause flexible elongated element 14 to flex. As shown in accompanying FIGS. 4-6 bending elements 16 and 18 each comprise a wound coil 35 having a magnet 37 coaxially therein. As electrical energy is applied to wound coils 35, magnets 37 are induced to move against flexible member 14, thereby inducing vibrational energy thereto. Since bending elements 16 and 18 (more specifically in this embodiment magnets 37) are oriented orthogonally to one another and in physical contact with elongated element 14, they cause elongated element 14 to move orthogonally as each of them is caused to move longitudinally within coil 35 (vibrate) by the application of electrical energy thereto. Such orthogonal movement of elongated element 14 induces a generally orbital movement to tip 15 as previously depicted in FIG. 2 by arrow 17. Since, as described more fully below, the phase of the energy induced to vibrate bending elements 16 and 18 can be reversed, tip 15 can be rotated in two opposite generally orbital paths as depicted by the two directional arrow shown in FIG. 2. This ability to reverse the generally orbital rotation of tip 15 is of particular use in biopsy procedures where the ability to reverse the rotation of tip 15 allows for the acquisition of relatively larger samples of tissue without relocation of tip 15 in the tissue target. Tip motion, as just described, may ease needle penetration, and/or fluid diffusion through tissue during injection procedures, and also provide tissue structure stimulation during specific procedures such as stimulation.

Electrical energy is imparted to bending elements 16 and 18 from batteries 50 and 52 (or similar energy providing drivers) via circuit board 52, with connection between bending elements 16 and 18 and batteries 38 and 40 being initiated by depression of switch 42. The frequency of the vibration of bending elements 16 and 18 as induced by the application of varying impulses of electrical energy from batteries 50 and 52 is controlled by the action of circuit board 54 that alters the frequency of vibration of bending elements 16 and 18 by varying the electrical energy supplied thereto from batteries 38 and 40. Circuit board 54 includes appropriate circuitry to provide: frequency, amplitude, waveform and phase inversion of the electronic signals transmitted to bending elements 16 and 18. Phase inversion will induce reversal of the direction of generally orbital movement 17 of tip 15 as depicted schematically in FIG. 2. The design and fabrication of such frequency, amplitude and waveform generator circuitry is well known in the art and no further description thereof is required herein to allow the skilled artisan to successfully practice the present invention.

Flexible elongated member 14 preferably comprises a needle of hollow shape. Such a hollow configuration that includes an elongated passage 41 running the entire interior length of elongated member 14, permits the injection of fluids, substances, mixtures or materials such as a radioactive seed in the case of brachytherapy treatment or the extraction/aspiration of tissue or the like in the case of a biopsy. In the latter instance, in order that elongated member/hollow needle 14 can be inserted to a point of interest, for example a tumor or the like, without preliminary collection of tissue that is not of interest during insertion, a stylet 46 is inserted through aperture 30 in hub 28 and passes through interior passage 41 of needle/elongated member 14 to plug interior passage 41 of needle 14 until it has reached the point of aspiration whereupon stylet 46 is withdrawn and aspiration, biopsy etc. performed.

Batteries 38 and 40 are preferably lithium/alkaline batteries because of their long life and consistent voltage output up to the point of failure.

The magnets utilized in bending elements 16 and 18 are preferably neodymium magnets of the same radial length as coils 35 with the tips thereof extending beyond the surfaces of coils 35 proximate flexible member 14 as shown in the accompanying drawings. It is also beneficial for, but not critical to, the successful practice of the present invention that the poles of magnets 37 be opposing, i.e. one of the magnets has its north pole addressing flexible member 14 and the other has its south pole addressing flexible member 14. such an arrangement alleviates the problem of the two magnets "working" against each other during operation thereby reducing the amount of energy needed to power them in the energized cycle.

It is contemplated that any number of devices in addition to stylet 46 can be inserted into interior passage 41, for the accomplishment of a variety of procedures. For example, in order to minimize the need for multiple needle or flexible element patient insertions and to simplify manufacturability of the small diameter tubes and stylets used in conjunction with device 10, an array of inserts coaxial with flexible member 14 but of a smaller diameter than passage 41 or of decreasing diameter can be simultaneously inserted into flexible member 14.

Figure 7:
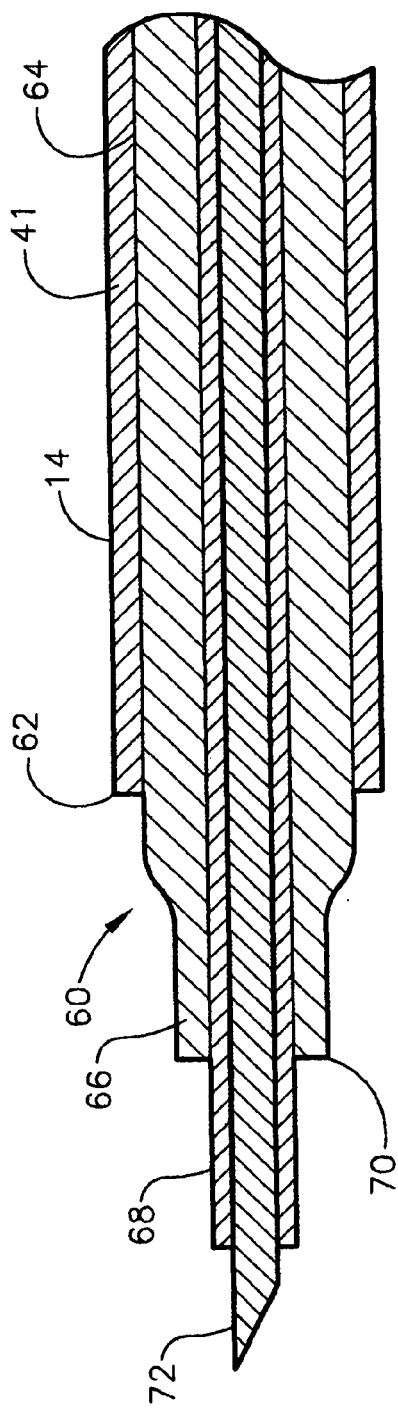
FIG. 7 is a cross-sectional view of an alternative preferred embodiment of the core of the ultrasonically detectable device of the present invention.
Figure 8:
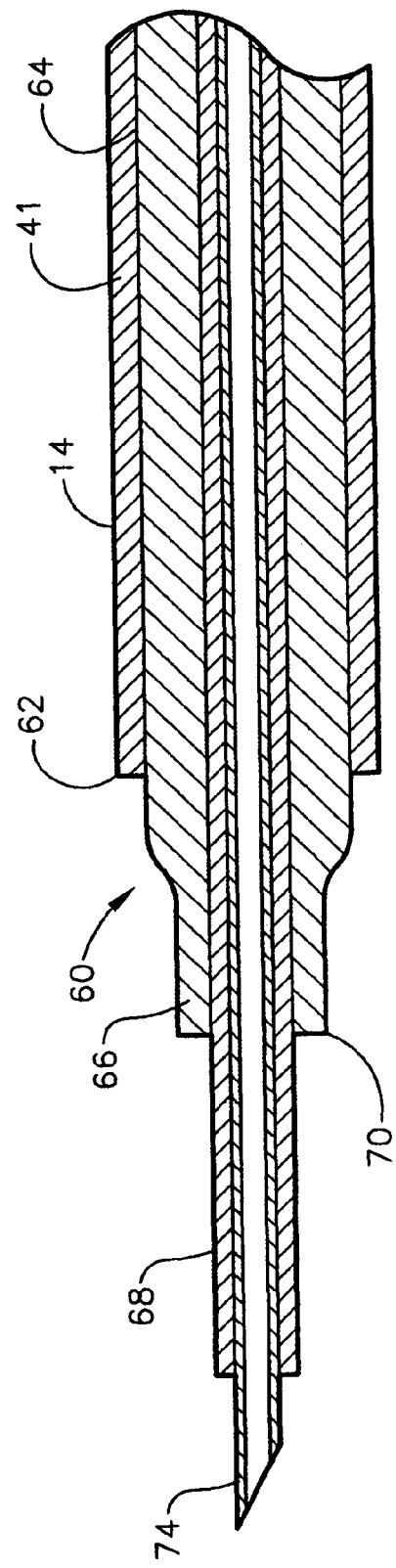
FIG. 8 is a cross-sectional view of a modification of the alternative preferred embodiment of the core of the ultrasonically detectable device of the present invention.

For example, referring now to accompanying FIGS. 7 and 8 that depict alternative highly preferred embodiments of the ultrasonically detectable device of the present invention, in the embodiment depicted in FIG. 7, flexible elongated member 14 having passageway 41 therein is truncated or shortened and a necked down insert 60 that extends beyond the terminus 62 of truncated flexible elongated member 14 is inserted through passageway 41. Necked down insert 60 includes a larger diameter portion 64 and a smaller diameter portion 66. As will be apparent to the skilled artisan, larger portion 64 of necked down insert 60 may extend to terminus 62 or alternatively be encompassed within passageway 41. As previously stated, it is critical to the successful practice of the present invention that the outer diameter of larger diameter portion 64 fit snuggly inside of passageway 41, i.e. engage the inner wall of truncated flexible elongated member 14 so that vibrational energy is transmitted undiminished from truncated flexible elongated member 14 to necked down insert 60. Further in accordance with the embodiment depicted in FIG. 7, stylet 72 that extends beyond the terminus 70 of necked down insert 60 is inserted through coaxial tube 68 that extends through necked down portion 66. Again, it is critical to the successful practice of the present invention that the outer wall of stylet 72 be in intimate contact with the inner wall of coaxial tube 68 to assure proper transmission of vibrational energy from necked down portion 66 to stylet 72 via coaxial tube 68. In this manner, stylet 72 can be used to "cut" a channel into the appropriate location within the body without insertion of any portion of truncated flexible elongated member 14 into the body. As shown in FIG. 8, a tissue sample can then be extracted after stylet 72 is removed, and an interventional needle-like instrument or device 74 inserted into coaxial tube 68 for the performance of tissue extraction through the aperture previously "cut" by stylet 72. Again, it is critical to the successful practice of the invention that the outer circumferences of coaxial tube 72 and needle-like instrument or device 74 be in intimate contact with the inner wall of coaxial tube 68 and each other so that vibrational energy is transmitted to coaxial tube 72 and needle-like instrument or device 74 substantially undiminished.

Similarly, it is contemplated that stylet 46/72 or any other device inserted into passage 41, which has some degree of "shape memory", can be suitably bent prior to insertion into passage 41 such that upon exit from tip 15 it "recovers" its bent shape thereby extending the reach of the device in the tissue into which flexible member 14 has been inserted.

Figure 3:
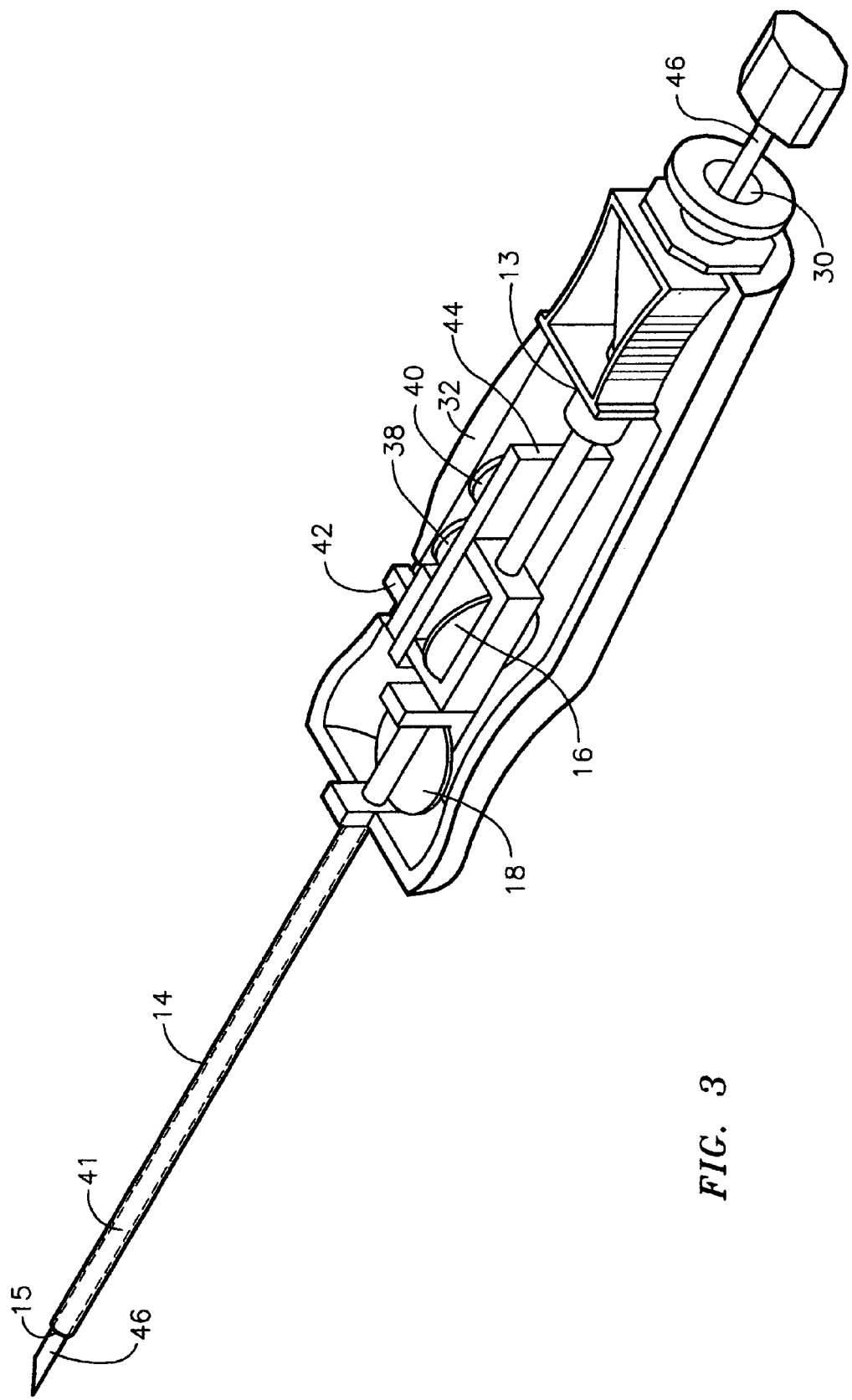
FIG. 3 is a cutaway view of the ultrasonically detectable device of the present invention having a stylet inserted therein.

Whatever device(s) is/are inserted into passageway 41 (such as the stylet depicted in FIGS. 3 and 6, (as well as FIG. 7 described below) it is critical to the successful practice of the present invention that such device(s) are in intimate contact with the circumferential wall of passageway 41 to assure that vibrational energy imparted to flexible member 14 is consistently and without loss of energy transmitted to the inserted device.

There has thus been described an ultrasonically detectable probe or interventional device that can be used for a wide range of interventional procedures including, but not limited to, the acquisition of biopsy samples through aspiration or the like as well as the placement of or precise deposition of, for example, drugs, fluids microencapsulated drugs, substances, mixtures thereof or radioactive seeds or the like of animal or human tissue lesions or tumors. The interventional device or probe described herein is inexpensive to manufacture, can be made disposable and is readily adaptable to medical treatment procedures already in use, all while being viewable using existing ultrasonic detection systems.

While various of the elements of the interventional device of the present invention have been described in the context of certain preferred embodiments such as those depicted in the accompanying Figures, it will be readily apparent to the skilled artisan that a variety of basic modifications/alterations of these specific embodiments are readily determinable. For example, a plurality (greater than two) electrically activated orthogonally oriented bending members oriented at any of a wide variety of angles could be used in the successful practice of the present invention.

In use, after insertion of device 10, stylet 45, 46 or 68 or some other suitable probe into a patient at a suitable location, activation by depression of switch 42 initiates a linear sweep sequence controlled by circuit board 54 at a sweep rate lasting less than about 1/10 of a second over the range of vibrational frequencies of from about 300 and about 800 HZ. The linear sweep is preferably performed over a period of between about 10 and about 40 milliseconds over the frequency range of from about 600 and about 750 Hz. Such a vibration scheme provides a readily ultrasonically detectable signal in conventional ultrasonic detection systems.

As the invention has been described, it will be apparent to those skilled in the art that the same may be varied in many ways without departing from the spirit and scope of the invention. Any and all such modifications are intended to be included within the scope of the appended claims.

What is claimed is:

1. An interventional medical device for use with a motion-sensitive ultrasonic imaging system comprising:
   a) a flexible elongated member having a tip at one extremity thereof and a hub at the opposing extremity thereof;
   b) a flexing mechanism mechanically coupled to the flexible elongated member, the flexing mechanism comprising a two axis flexing mechanism configured to induce an orbital movement within the flexible elongated member; and
   c) a mechanism configured for controlled spread-spectrum, quadrature-phased electrical excitation of the flexing mechanism and the flexible elongated member mechanically coupled thereto wherein the spread-spectrum electrical excitation comprises a linear sweep repeated at a rate of less than $1/10$ second over an audible frequency range, wherein continual visualization of the elongated member is maintained without operator adjustment and visualization of the elongated member at any rotational position is maintained without operator adjustment.

2. The interventional medical device of claim 1 wherein the flexible elongated member comprises a hollow needle.

3. The interventional medical device of claim 1 wherein the two-axis flexing mechanism comprises a pair of orthogonally oriented piezoelectric discs.

4. The interventional medical device of claim 3 wherein the mechanism for controlled electrical excitation of the two-axis flexing mechanism comprises:
   a) an energy source; and
   b) an electronic controller electrically connected to the energy source and the two-axis flexing mechanism for controlling the frequency, amplitude, waveform and phase of electrical energy transmitted to the two-axis flexing mechanism.

5. The interventional medical device of claim 4 wherein the mechanism for controlled electrical excitation of the two-axis flexing mechanism is capable of reversing the phase of the electrical energy transmitted to the piezoelectric discs thereby reversing the direction of the orbital movement of the flexible elongated member.

6. The interventional medical device of claim 2 wherein the two-axis flexing mechanism comprises a pair of orthogonally oriented piezoelectric discs.

7. The interventional medical device of claim 6 wherein the mechanism for controlled electrical excitation of the two-axis flexing mechanism comprises:
   a) an energy source; and
   b) an electronic controller electrically connected to the energy source and the two-axis flexing mechanism for controlling the frequency, amplitude, waveform and phase of electrical energy transmitted to the two-axis flexing mechanism.

8. The interventional medical device of claim 7 wherein the mechanism for controlled electrical excitation of the two-axis flexing mechanism causes the flexible elongated member to move in an orbital path.

9. The interventional medical device of claim 8 wherein the mechanism for controlled electrical excitation of the two-axis flexing mechanism is capable of reversing the phase of the electrical energy transmitted to the piezoelectric discs thereby reversing the direction of the orbital movement of the flexible elongated member.

10. The interventional medical device of claim 1 wherein the two-axis flexing mechanism comprises a pair of orthogonally oriented assemblies each comprising a wound coil surrounding a coaxial magnet whose longitudinal movement is driven by electrically energizing the coil.

11. The interventional medical device of claim 10 wherein the mechanism for controlled electrical excitation of the two-axis flexing mechanism comprises:
    a) an energy source; and
    b) an electronic controller electrically connected to the energy source and the two-axis flexing mechanism for controlling the frequency, amplitude, waveform and phase of electrical energy transmitted to the two-axis flexing mechanism.

12. The interventional medical device of claim 11 wherein the mechanism for controlled electrical excitation of the two-axis flexing mechanism causes the flexible elongated member to move in an orbital path.

13. The interventional medical device of claim 12 wherein the mechanism for controlled electrical excitation of the two-axis flexing mechanism is capable of reversing the phase of the electrical energy transmitted to the pair of orthogonally oriented assemblies thereby reversing the direction of the orbital movement of the flexible elongated member.

14. The interventional medical device of claim 1 further including a housing encompassing the interventional medical device, said housing having an aperture therein through which the flexible elongated member penetrates and an elastomeric constraint about the flexible elongated member that forms a seal between the flexible elongated member and the aperture.

15. The interventional medical device of claim 3 further including a housing encompassing the interventional medical device, said housing having an aperture therein through which the flexible elongated member penetrates and an elastomeric constraint about the flexible elongated member that forms a seal between the flexible elongated member and the aperture.

16. The interventional medical device of claim 10 further including a housing encompassing the interventional medical device, said housing having an aperture therein through which the flexible elongated member penetrates and an elastomeric constraint about the flexible elongated member that forms a seal between the flexible elongated member and the aperture.

17. The interventional medical device of claim 1 further including a necked down insert inserted into the flexible elongated member, the necked down insert including a first extremity of larger diameter proximate the hub and a second extremity of a smaller diameter remote from the hub and extending beyond the tip of the flexible elongated member.

18. The interventional medical device of claim 17 further including a stylet or other hollow needle or needle like instrument or probe inserted into the necked down insert, the stylet or other hollow needle or needle like instrument or probe having a first extremity proximate the hub and a second extremity remote from the hub extending beyond the second extremity of the necked down insert.

* * * * *